United States Patent
Klausen

(10) Patent No.: US 10,123,863 B2
(45) Date of Patent: Nov. 13, 2018

(54) MECHANISM FOR APPLYING HIGH RADIAL FORCE IN LESS-ELASTIC MEDICAL DEVICES

(71) Applicant: Cook Medical Technologies LLC, Bloomington, IN (US)

(72) Inventor: Kasper Klausen, Lille Skensved (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 618 days.

(21) Appl. No.: 14/666,728

(22) Filed: Mar. 24, 2015

(65) Prior Publication Data

US 2015/0272752 A1 Oct. 1, 2015

Related U.S. Application Data

(60) Provisional application No. 61/971,836, filed on Mar. 28, 2014.

(51) Int. Cl.
*A61F 2/01* (2006.01)

(52) U.S. Cl.
CPC ........... *A61F 2/01* (2013.01); *A61F 2002/011* (2013.01); *A61F 2002/016* (2013.01); *A61F 2230/0023* (2013.01); *A61F 2230/0058* (2013.01); *A61F 2230/0067* (2013.01)

(58) Field of Classification Search
CPC .................. A61F 2/01; A61F 2002/011; A61F 2002/016; A61B 17/12022; A61B 17/12027; A61B 17/12131; A61B 17/12136; A61B 17/1204; A61B 17/12104; A61B 17/12109; A61B 17/12122; A61B 17/1214; A61B 17/12154; A61B 17/12159; A61B 17/12163; A61B 17/12168; A61B 17/22
See application file for complete search history.

(56) References Cited

U.S. PATENT DOCUMENTS

| 5,133,733 A | | 7/1992 | Rasmussen et al. |
| 5,370,657 A | * | 12/1994 | Irie ........................ A61F 2/01 606/200 |
| 5,626,605 A | * | 5/1997 | Irie ........................ A61F 2/01 606/200 |
| 5,709,704 A | | 1/1998 | Nott et al. |
| 5,733,294 A | | 3/1998 | Forber et al. |
| 6,245,103 B1 | | 6/2001 | Stinson |
| 6,258,026 B1 | | 7/2001 | Ravenscroft et al. |

(Continued)

FOREIGN PATENT DOCUMENTS

WO  WO 00/64374  11/2000

*Primary Examiner* — Ryan J Severson
*Assistant Examiner* — Christian Knauss
(74) *Attorney, Agent, or Firm* — Brinks Gilson & Lione

(57) ABSTRACT

A biodegradable device capable of producing a high radial force is described. Such a force will be created in devices made of relatively inelastic materials that are to be deployed to the vasculature or a body cavity in a patient. As the halves of the devices move together subject to a longitudinal force, at the point where they are in contact and unable to move closer together in the longitudinal direction, a radial force is created. The devices may have a tension element that assists in bringing the device halves together and which may partially and optionally remain within the body of the device.

12 Claims, 5 Drawing Sheets

(56) References Cited

U.S. PATENT DOCUMENTS

| | | |
|---|---|---|
| 6,443,972 B1 | 9/2002 | Bosma et al. |
| 6,663,664 B1 | 12/2003 | Pacetti |
| 6,755,867 B2 | 6/2004 | Rousseau |
| 6,755,868 B2 | 6/2004 | Rousseau |
| 6,972,025 B2 | 12/2005 | WasDyke |
| 7,347,869 B2 | 3/2008 | Hojeibane et al. |
| 8,152,831 B2 | 4/2012 | Magnuson et al. |
| 8,162,970 B2 | 4/2012 | Gilson et al. |
| 8,182,508 B2 | 5/2012 | Magnuson et al. |
| 8,236,039 B2 | 8/2012 | Mackiewicz |
| 8,257,426 B2 | 9/2012 | Gomez et al. |
| 8,348,992 B2 | 1/2013 | Brown et al. |
| 8,449,598 B2 | 5/2013 | Ainsworth et al. |
| 2002/0193828 A1 | 12/2002 | Griffin et al. |
| 2006/0025852 A1 | 2/2006 | Armstrong et al. |
| 2006/0212055 A1 | 9/2006 | Karabey et al. |
| 2007/0032816 A1 | 2/2007 | O'Connell et al. |
| 2008/0281350 A1 | 11/2008 | Sepetka et al. |
| 2012/0083823 A1 | 4/2012 | Shrivastava et al. |
| 2012/0143238 A1 | 6/2012 | Sogard |
| 2012/0221040 A1 | 8/2012 | Eggers |

\* cited by examiner

MECHANISM FOR APPLYING HIGH RADIAL FORCE IN LESS-ELASTIC MEDICAL DEVICES

CROSS REFERENCE TO RELATED APPLICATIONS

This application claims the benefit of U.S. Provisional Patent Application No. 61/971,836, filed on Mar. 28, 2014, the entire contents of which is hereby incorporated by reference.

BACKGROUND

The present invention relates to medical devices. More particularly, the invention relates to a device made from a less-elastic or biodegradable material that is capable of producing a relatively large radial force in order to prevent device migration and/or maintain patency in a body vessel.

Filtering devices are percutaneously placed in body vessels of a variety of medical patients, including but not limited to trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs. In some cases, a filtering device can be deployed in the vena cava of a patient when, for example, anticoagulant therapy is contraindicated or has failed.

Typically, filtering devices are permanent implants, each of which remains implanted in the patient for life, even though the condition or medical problem that required the device has passed. However, it can be desirable to remove unneeded implants when the medical risk has passed.

In some cases, filters have not been considered removable from a patient due to the likelihood of endotheliosis of the filter or fibrous reaction matter adherent to the endothelium during treatment. After deployment of a filter in a patient, proliferating intimal cells begin to accumulate around the filter struts which contact the wall of the vessel. After a length of time, such ingrowth prevents removal of the filter without risk of trauma, requiring the filter to remain in the patient.

Even in cases where removal of the implant or device is possible, a second surgical procedure and the attendant risks can be undesirable. As such, removal of the device, even when possible, is sometimes not elected.

Medical devices, including filtering devices, can be made from biodegradable materials. These devices have the advantage of functioning for a limited time and then slowly get absorbed by the patient's body, obviating a second surgery for removal of the device. However, unlike permanent devices made from elastic materials like spring steel or shape-memory metals, devices made from biodegradable materials can lack mechanical properties and in some cases make suboptimal contact with vessel walls, thereby risking migration.

It is desirable to use a medical device made of a biodegradable material which can also produce a strong radial force against the wall of a body vessel.

SUMMARY

According to a first aspect of the present invention, a medical device for implantation in a body vessel is provided comprising a first collet comprising a first tube and a first cap, the first tube having a first tube end and extending to a second tube end, and a lumen formed through the first tube end to the second tube end, the first cap having an interior surface and being attached to the first tube end; a first device half having a proximal end and a distal end opposite the proximal end and defining a longitudinal axis therethrough, the first device half comprising a plurality of struts having a first arm and a second arm connected to the first arm, each first arm having a first end disposed at the proximal end of the first device half, the first arm extending angled away from the longitudinal axis to a second end, each second arm having a third end connected to the second end of the first arm and extending proximally and substantially parallel to the longitudinal axis to a fourth end, a locking element being disposed on at least one first arm, the second tube end of the first tube being attached to the first arms at the proximal end so that the first ends are disposed within the lumens of the first tube; a second collet comprising a second tube and a second cap, the second tube having a first tube end and extending to a second tube end, and a lumen formed through the first tube end to the second tube end, the second cap having an aperture formed therethrough and being attached to the first tube end; a second device half having a proximal end and a distal end opposite the proximal end and defining a longitudinal axis therethrough, the second device half comprising a plurality of struts having a first arm and a second arm connected to the first arm, each first arm having a first end disposed at the distal end of the second device half, the first arm extending angled away from the longitudinal axis to a second end, each second arm having a third end connected to the second end of the first arm and extending distally and substantially parallel to the longitudinal axis to a fourth end, a locking element being disposed on at least one first arm, the second tube end of the second tube being attached to the first arms at the distal end so that the first ends are disposed within the lumens of the second tube; and a tensioner having a first end and a second end, the first end of the tensioner being attached to the interior surface of the first cap, the tensioner extending to the second end through the aperture of the second collet.

In another embodiment, a medical device is provided comprising a first collet comprising a first sleeve and a first cap, the first sleeve comprising a tube having a first tube end, a second tube end, and a lumen formed therethrough, the first cap having an interior surface, the first cap being attached to the first tube end of the first sleeve; a first device half having a longitudinal axis and comprising a plurality of struts, each strut comprising a first arm having a first end and a second end, the first arm extending substantially parallel to the longitudinal axis and from the first end to the second end, the first ends of the first arms being disposed through the second tube end and within the lumen of the first sleeve and attached substantially circumferentially about the interior surface of the first cap, each strut having a pair of secondary arms each having a first end and a second end, the first end of a secondary arm being attached to the second end of a first arm, the secondary arms being arranged to form a substantially cylindrical device half; a second collet comprising a second sleeve and a second cap, the second sleeve comprising a tube having a first tube end, a second tube end, and a lumen formed therethrough, the second cap having an interior surface and an aperture formed therethrough in fluid contact with the second lumen, the second cap being attached to the first tube end of the second sleeve; a second device half opposite and in alignment with the first device half, the second device half having a longitudinal axis and comprising a proximal end and a distal end, the second device half comprising a plurality of struts, each strut comprising a first arm having a first end and a second end, the first arm extending substantially parallel to the longitudinal axis and from the first end to the second end, the first ends of the first arms being disposed through the second tube end and within the lumen of the second sleeve and attached substantially circumferentially about the interior surface of the second cap, each strut having a pair of secondary arms each having a first end and a second end, the first end of a secondary arm being attached to the second end of a first arm, the secondary arms being arranged to form a substantially cylindrical device half; and a tensioner having a first end and a second end, the first end of the tensioner being attached to the interior surface of the first cap, the tensioner extending to the second end through the aperture of the second collet.

According to another aspect of the present invention, there is provided a medical device comprising a first collet comprising a first sleeve and a first cap, the first sleeve comprising a tube having a first tube end, a second tube end, and a lumen formed therethrough, the first cap having an interior surface, the first cap being attached to the first tube end of the first sleeve; a first device half having a longitudinal axis and comprising a plurality of struts, each strut comprising a first arm having a first end and a second end, the first arm extending substantially parallel to the longitudinal axis and from the first end to the second end, each strut having a pair of secondary arms each having a first end and a second end, the first end of a secondary arm being attached to the second end of a first arm, the second ends of the secondary arms being disposed through the second tube end and within the lumen of the first sleeve and attached substantially circumferentially about the interior surface of the first cap, the first arms being arranged to form a substantially cylindrical device half; a second collet comprising a second sleeve and a second cap, the second sleeve comprising a tube having a first tube end, a second tube end, and a lumen formed therethrough, the second cap having an interior surface and an aperture formed therethrough in fluid contact with the second lumen, the second cap being attached to the first tube end of the second sleeve; a second device half opposite and in alignment with the first device half, the second device half having a longitudinal axis and comprising a plurality of struts, each strut comprising a first arm having a first end and a second end, the first arm extending substantially parallel to the longitudinal axis and from the first end to the second end, each strut having a pair of secondary arms each having a first end and a second end, the first end of a secondary arm being attached to the second end of a first arm, the second ends of the secondary arms being disposed through the second tube end and within the lumen of the second sleeve and attached substantially circumferentially about the interior surface of the second cap, the first arms being arranged to form a substantially cylindrical device half; and a tensioner having a first end and a second end, the first end of the tensioner being attached to the interior surface of the first cap, the tensioner extending to the second end through the aperture of the second collet.

Further aspects, features, and advantages of the invention will become apparent from consideration of the following description and the appended claims when taken in connection with the accompanying drawings.

BRIEF DESCRIPTION OF THE DRAWINGS

Preferred embodiments of the present invention are described below, by way of example only with reference to the accompanying drawings in which.

DETAILED DESCRIPTION

It is to be understood that the figures are schematic and do not show the various components to their actual scale. In many instances, the figures show scaled up components to assist the reader.

In this description, when referring to a deployment assembly or a medical device, the term distal is used to refer to an end of a component which in use is furthest from the surgeon during the medical procedure, including within a patient. The term proximal is used to refer to an end of a component closest to the surgeon and in practice in or adjacent an external manipulation part of the deployment or treatment apparatus.

"Substantially" or derivatives thereof as used herein will be understood to mean significantly or in large part. The terms "substantially" or "about" used herein with reference to a quantity includes variations in the recited quantity that are equivalent to the quantity recited, such as an amount that is equivalent to the quantity recited for an intended purpose or function.

A component which is "angled away" from another component may or may not share a vertex with the component from which it is angled away. The angle formed when a component is "angled away" from another component is a non-zero angle; that is, the component which is angled away does not run parallel to, or entirely overlie, the component from which it is angled away.

Figure 1A:
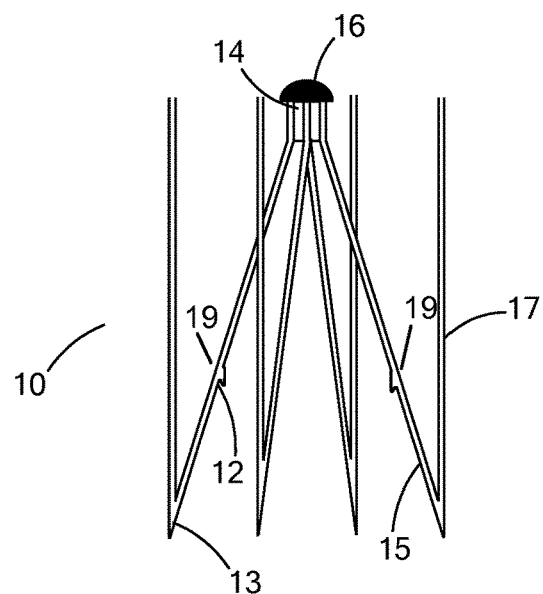
FIG. 1A is a side view of a biodegradable device filter half in accordance with one embodiment of the present invention.

An example of a medical device half made from a biodegradable material is illustrated in FIG. 1A. Device half 10 comprises a plurality of struts 12 which can have first arm 15 and second arm 17. In the embodiment illustrated, the device half comprises four struts, but a device with two struts, three struts, five struts, six struts, eight struts, ten struts, twelve struts, or another number of struts is also possible in accordance with the principles of this invention.

The device half 10 may have a substantially conical shape. A conical shape has an open end and an apical end.

In this case, the apical end would comprise the collet 14 at which the struts 12 converge. The collet 14 surrounds a first end of each strut 12.

Each first arm 15 has a first end and a second end. The first end meets and is attached to, or disposed within, collet 14. Such attachment may be fixed attachment, or unfixed attachment in which the end of the strut is disposed within the collet and held there by radial forces, rather than by a securing mechanism such as adhesive, glue, soldering, or the like. The second end of first arm 15 is attached to second arm 17 at strut arm junction 13. In one embodiment, the overall shape of strut 12 is a V-shape or a triangular shape. Collet 14 has a cap portion 16.

In another embodiment, the struts 12 comprise only a single strut arm such as first arm 15.

In one embodiment of the device, the struts 12 act to filter emboli in the vasculature of a patient who is being treated. The first arm 15 or the second arm 17, or both, may be in contact with a vessel wall of the patient.

Figure 1B:
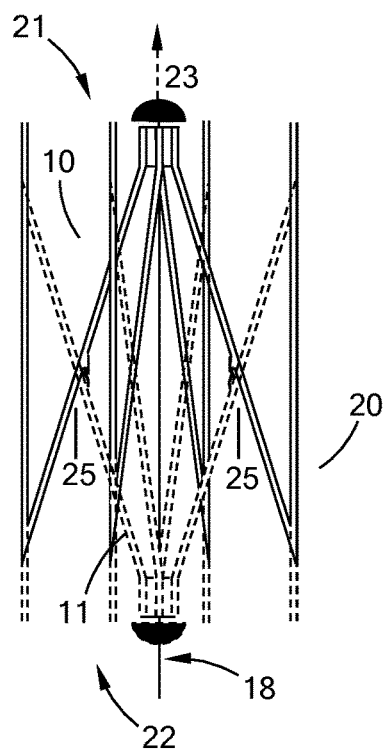
FIG. 1B is a side view of two biodegradable device filter halves forming a single filter device in accordance with one embodiment of the present invention.

In one aspect, the device comprises two device halves. Turning now to FIG. 1B, two device halves 10 and 11 interacting with one another are arranged to form the full device 20. The device 20 has a proximal end 21 and a distal end 22, although in many cases the device is symmetrical and the proximal end 21 may be implanted in the patient distally and the distal end 22 may be implanted in the proximal direction. Imparting directionality to the device 20 may be tensioner 18. The tensioner element 18 is attached to a first collet 14, in some embodiments on collet head 16. The collet may comprise a head or cap portion attached to a sleeve, which is hollow tube. The cap portion may simply cover and close the open end of the tube or sleeve of the collet. The cap portion has an interior, disposed facing the lumen of the tube, and an exterior opposite the interior. The interior of the cap provides a good surface for the attachment of a tensioner. In some cases the tensioner may be attached by an adhesive. In another embodiment, the cap may have a loop formed on it on the interior side, and the tensioner may be threaded through the loop and tied to it. In some embodiments, the tensioner 18 overlies the longitudinal axis 23 of the device 20. In some embodiments, the tensioner 18 passes through a hole 33 that is formed through the second collet of device 20. The first collet and the second collet are provided in one embodiment in opposite orientations to one another; that is, the head or cap portions of the collets represent the extreme proximal and distal ends of the device 20.

In one embodiment, the distal end 21 of the device 20 is the end where a collet is attached in a fixed fashion to the tensioner 18, and the proximal end is the end where the tensioner 18 passes through a hole or channel 33 which is formed or bored through a collet.

The points where first device half 10 and second device half 11 come into contact during deployment are known as locking zones 25. In the embodiment of FIGS. 1-2, the locking zones 25 are made possible by the presence of locking bumps 19. The general way in which the device provides a radial force, which allows for better patency and increased contact with the vessel wall, is that the tensioner 18 is pulled in through the hole 33 in the second collet 14 at the proximal device end 22 and as a force is applied along the longitudinal axis 23, the device halves come together. In one embodiment, this is due to the first device half 10, which is fixedly attached to the tensioner 18, moves in the proximal direction. The device halves 10 and 11 then contact one another at their locking zones 25 via locking bumps 19. At this point, the device halves 10 and 11 can no longer move together along the longitudinal axis 23. As a result, the force applied in the longitudinal direction results in a compression of the device halves 10 and 11 as they experience a greater force against one another. This causes an expansion in the radial direction, substantially normal to the longitudinal axis. Such radial expansion can occur either with or without a substantial change in the length of the device along a lengthwise dimension (that is, parallel to the longitudinal axis of the device 20.) This, in turn, provides an increased amount of contact with the vessel wall, and therefore better patency and higher radial force of the device within the vasculature of the patient to be treated.

The shape of a strut 12 can be substantially V-shaped or triangular. Optionally, the strut 12 may have a first portion which is substantially parallel to the longitudinal axis 23. A strut 12 may also have an optional second portion which is substantially parallel to the longitudinal axis. These first and second portions may be substantially parallel to one another. The first portion may have the ability to more conveniently be fit into a collet 14 which has a central lumen 38. The second portion can provide a relatively small area of greater contact with a vessel wall during initial deployment.

Optionally, the strut 12 has a locking bump 19. This locking bump provides a greater area of contact between the device halves 10 and 11. The locking bump can be employed in many designs of a device half but particularly in embodiments wherein the struts 12 consist of only a single arm.

FIG. 2 shows how the device halves 10 and 11 can come together to form device 20 in a method of deployment. The method of capturing thrombi in a body vessel may comprise the steps of deploying a filter. such that an arm of a strut is positioned against the internal wall of a vessel, the filter having a first device half and second device half which can move independently of each other along the longitudinal axis of the device. In one embodiment, the proximal (closest to the operator) device half has been more securely engaged to the internal wall of the vessel than has the distal device half. The first half approaches, then contacts, the second device half. In one embodiment, portions of the first device half may even slide past parts of the second device half.

The first device half and the second device half each have a locking feature 19 on a portion of some of their struts. In depicted embodiments, the locking features 19 are shown on the first arms 15. The locking features of the device halves engage when the device halves are pushed or pulled together, such as when a tensioner fixed to the distal-most device end is pulled proximally. The medical device is able to expand in a radial direction after the locking features have engaged and upon application of further force which would otherwise push the device halves toward one another, but because the halves are interlocked, a force substantially normal to the direction of pulling is generated.

In one embodiment the tensioner 18 can be broken when a sufficient pulling force is applied thereto, with a shortened tensioner portion remaining connecting the first collet to the second collet. In general, the second collet will have a notch, a hole, or another similar feature into which the tensioner 18 can be positioned and secured. Then a further force can be applied, such as pulling against a wall of the collet, or simply pulling more forcefully on the tensioner 18 to snap it. In some embodiments, a knot may be tied in the tensioner 18 so that it can more easily be held by the notch or similar tensioner-retaining feature of the collet. In another embodiment, the tensioner may simply be thicker at this point, or may have another component, possibly made of a different material, which will catch in the notch of the second collet.

Figure 2A:
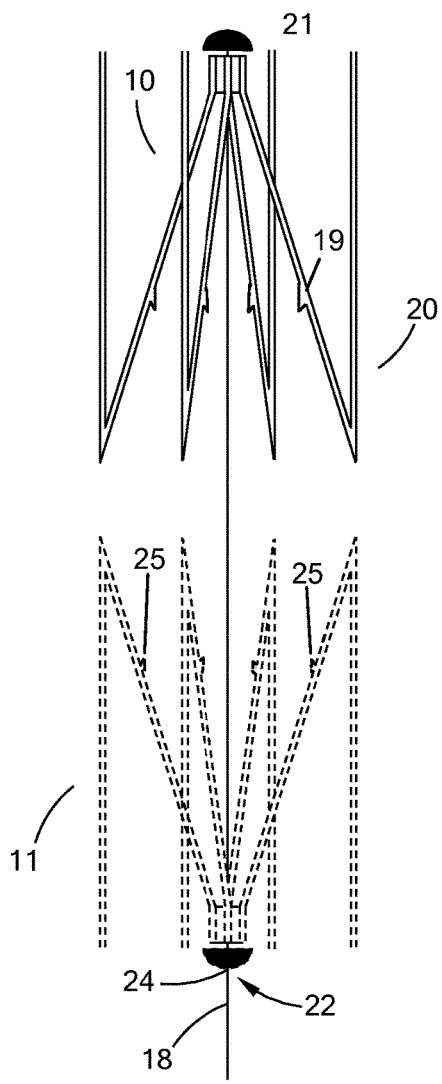
FIG. 2A-2D are side views of a biodegradable device filter being deployed in accordance with one embodiment of the present invention.

FIG. 2A shows how the device halves are spaced apart after initial delivery. A suitable deployment apparatus, such as an introducing catheter, optionally employing a wire guide, has been inserted into a body cavity of a patient to be treated. In some embodiments, this insertion is percutaneous. The device halves 10 and 11 are either entirely separate from one another or only in minimal contact with one another in this step. The tensioner 18 is seen attached to first collet 14 at the proximal end 21 of device half 10 and passing through an aperture of the second collet, which has as part of it tensioner point 24 at or near a hole or channel 33.

Figure 2B:
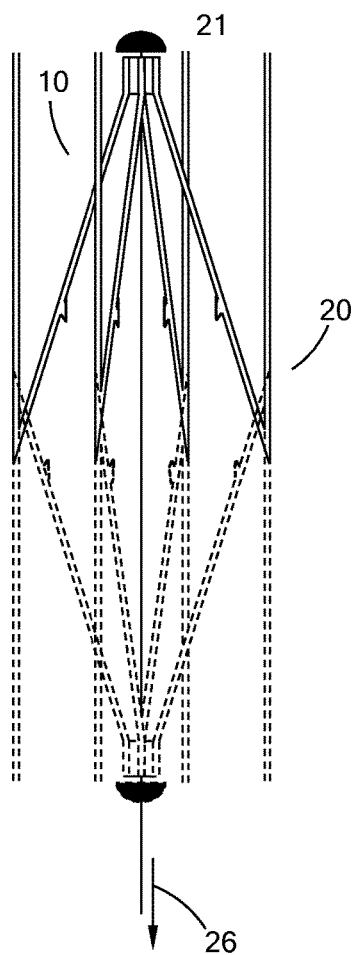

In FIG. 2B, the practitioner has applied a force 26 to the tensioner 18. In one embodiment, the tensioner 18 is long enough to pass through the delivery assembly and be manipulated by the interventionalist (or practitioner, physician, or surgeon.) In another embodiment, the tensioner 18 is has a shorter length but can be manipulated by the interventionalist by using a tool, such as forceps, that are used in conjunction with the delivery assembly and either contact the tensioner 18 within the delivery assembly or in the vasculature of the patient. At this step, the force 26 causes the two device halves 10 and 11 come together and begin to engage with one another.

Figure 2C:
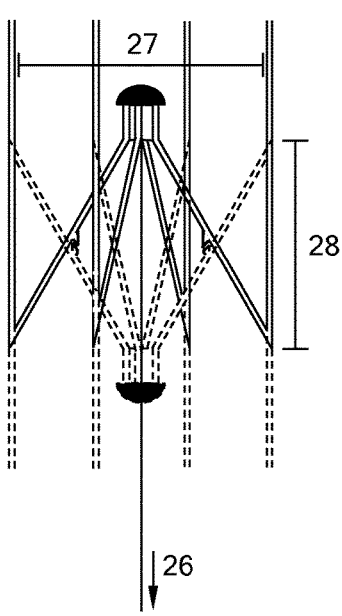

FIG. 2C shows the two device halves 10 and 11 fully engaged with one another as a result of the continued application of force 26. The locking zones 25 are now formed. In the embodiment illustrated, these locking zones 25 are initially strut arm junctions 13 and the portions of the opposite device half that the junctions 13 contacts. As the force 26 continues to act on the tensioner 18 and bring the device halves 10 and 11 in increased contact with one another, the lock zones 25 can become as extensive as the entire lengths of the struts 12, including the majority or entirety of first arms 15 and second strut arms 17. As shown in FIG. 2C, the device 20 has a first width dimension 27 and a first device length 28. The first width 27 is substantially the same width at this point in the method as at was in the step of FIG. 2A, but the first device length 28 has decreased as the force 26 has brought the device halves 10 and 11 together.

Figure 2D:
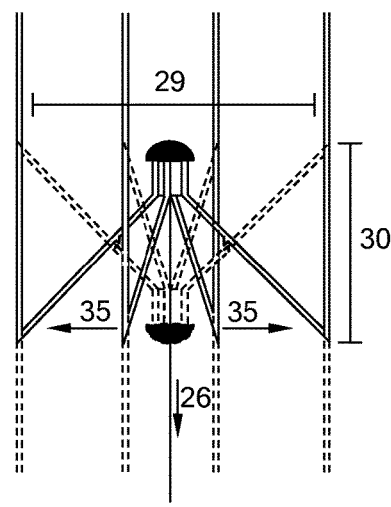

FIG. 2D shows the two device halves fully engaged with one another. After the locking zones 25 have met to their fullest extent, additional force 26 from continued pulling toward the interventionalist on tensioner 18 causes the device halves 10 and 11 to apply contact forces to one another such that the radial force 35 is exerted. This causes the device to expand to second device width 29, which is greater than first width 27. The second device length 30 may be less than first device length 28, or it may be substantially equal to (that is, not detectably different from) first device length 28. The device 20 now contacts the vessel wall and maintains patency of the device due to radial force 35 which continues to push the device outward relative to the longitudinal axis 23 of the device 20 while and after the device is implanted.

When the device 20 is fully deployed, the tensioner 18 can have a number of outcomes. The tensioner 18 can be made of a biodegradable material or a non-biodegradable substance. If the tensioner 18 is made of a non-degradable material, it must be removed entirely from the patient. This can be achieved by making the contact between the collet to which it is fixed at the proximal end 21 sufficiently strong to allow the device halves 10 and 11 to be pulled together and fully deployed but sufficiently weak to break this connection when the device has achieved its maximum patency configuration.

Contrarily, if the tensioner 18 is made of biodegradable material, it may be simply cut by the interventionalist and left within the patient to safely degrade. Alternatively, the tensioner contact zone 24 of the collet 14 may be notched, the notch having a width that is substantially similar to the width of the tensioner 18, that the tensioner can be positioned within. If the interventionalist makes a pulling motion at an angle to the longitudinal axis 23, the tensioner 18 will catch in the notch at the contact zone 24 and snap at that point. As a result, the tensioner 18 will have a shorter length, stretching only from proximal end 21 to distal end 22 of the device 20. The tensioner 18 will continue to force device halves 10 and 11 together and this force may assist in maintaining patency of the device 20 and preventing migration.

The tensioner 18 may be made of polycaprolactone (PCL). PCL is a biodegradable polyester which can be manufactured into a stretchable filament or strand. The tensioner may also be a copolymer of PCL and PLA in a predetermined ratio which will provide optimal stretchability and structural integrity. Over the course of deployment, the tensioner 18 will degrade, as will the remainder of the device.

Figure 3:
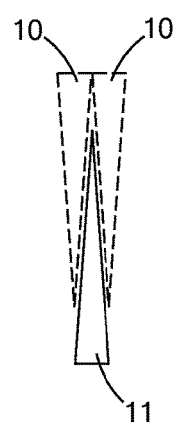
FIG. 3 is a view of three struts meeting in accordance with one embodiment of the present invention.

FIG. 3 illustrates how the struts 12 come together in a different embodiment of the device. The struts of device half 10 contact those of device half 11. The first arms 15 and second arms 17 of the strut of one device half are in contact with those of the other half, along a majority or the entirety of their lengths. This ensures interlocking of the halves and increases the chances of the halves creating radial force. In such an embodiment, the locking zone is represented by a large portion of the device arms, and no locking bump is present. In a preferred embodiment, the number of struts on the first device half 10 is equal to those of the second device half 11. In another embodiment, the first device half 10 has one more strut than device half 11, or one fewer. The interlocking triangular or V-shaped strut structure can provide a device 20 suitable for filtration of emboli which is substantially cylindrical in shape and suitable for maintaining patency in a vessel.

Figure 4A:
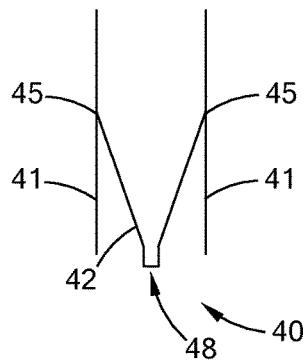
FIG. 4A-4B are views of strut configurations in accordance with further embodiments of the invention.
Figure 4B:
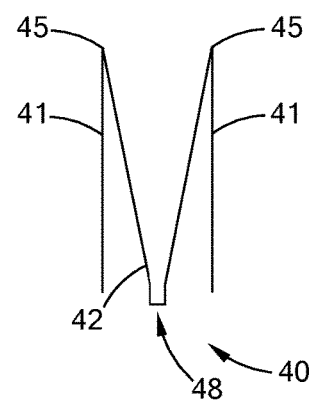

FIGS. 4A and 4B show embodiments of struts in accordance with further aspects of the invention of the present disclosure. In FIG. 4A, strut 40 has a pair of first strut arms 41 joined by triangular strut 42. The strut arms 41 meet triangular strut 42 at junctions 45. The triangular strut has an open portion and opposite that a vertex 48. FIG. 4B shows a similar configuration, but instead of junctions 45 being substantially midway down the length of strut arms 41, the junctions 45 at the ends of first strut arms 41. This gives an overall M-shape to the struts.

The struts may be individually cut or formed from the material and inserted within the collet. Alternatively, the struts may be cut from a tube of the material, such as by a laser.

Figure 5A:
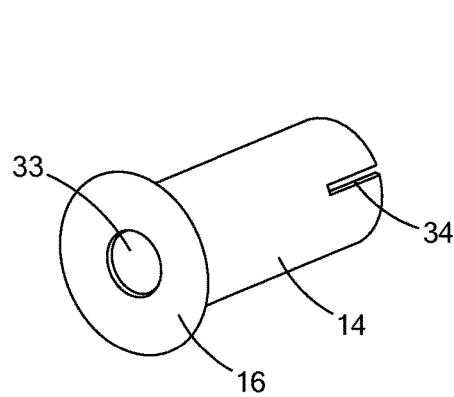
FIG. 5A-5B are perspective views of a collet in accordance with one embodiment of the present invention.
Figure 5B:
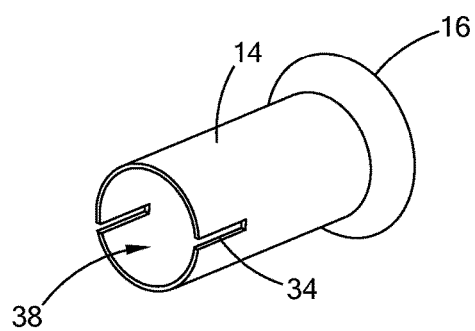

FIG. 5 is an illustration of the collet in accordance with an embodiment of the invention. The collet 14 has a head portion 16 and an aperture or channel 33 formed therethrough. Referring to FIG. 5B, the central lumen 38 of the collet 14 can be seen. The central lumen 38 has a diameter, which should be wide enough to accommodate some or all of the first ends of the struts 12. Optionally, collet 14 may include slots 34, which impart some flexibility in order to adjust for small variations in the struts that will be fit therein. The collet 14 should be made of relatively rigid material but also should be biodegradable.

The aperture of a collet, particularly a second collet, provides a space for the tensioner of a device to pass through. The interventionist pulls the tensioner to first bring the device halves together and then bring them into contact with one another, the device halves extending radially as an additional force is applied to the frame of the device by further pulling on the tensioner.

Figure 6A:
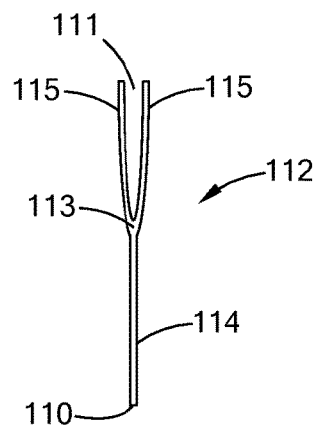
FIG. 6A-6B are views of forking struts in accordance with another embodiment of the present invention.
Figure 6B:
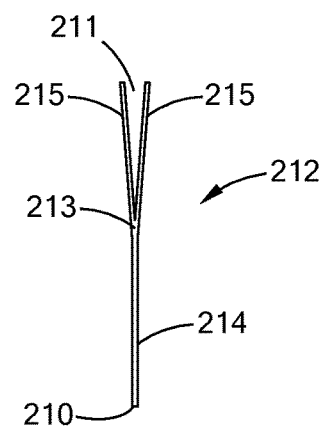

In FIGS. 6A and 6B, another embodiment of a strut is shown. The strut is forked or pronged. Strut 112 has an overall pronged shape, with a first arm 114 having first end (or first arm first end) 110 and extending to a second end (or first arm second end) at forking point 113. Two secondary strut arms (or first secondary arm and second secondary arm) 115 extend from a first end (or first second arm end) at forking point 113 to a second end (or second second arm end) at 111. The pronged strut structures may take a U-shape as in FIG. 6A, or a V-shape as in FIG. 6B. In the embodiment of FIG. 6B, the second strut arms 215 meet at forking point 213 at a sharp angle and then converge into first strut arm 214 at the first end 210. In one embodiment, the second strut arms may instead take on an overall U shape, as the secondary arms run parallel to one another for much of their lengths but bend curvedly toward the forking point.

Figure 6C:
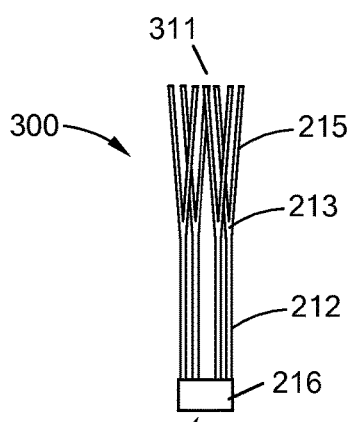
FIG. 6C-6D are views of device halves comprising forking struts in accordance with another embodiment of the present invention
Figure 6D:
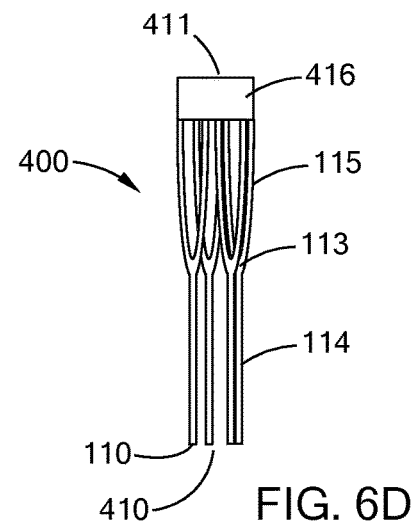

FIGS. 6C and 6D show device halves 300 and 400 respectively which illustrate one way in which the pronged struts of FIGS. 6A and 6B can be arranged in a device half. In the embodiment shown in FIG. 6C, the struts are arranged such that the first ends of the primary struts are constrained within the collet and the second ends of the secondary struts are free.

In the embodiment of FIG. 6D, the struts may instead be arranged such that the second ends 215/115 are contained within an empty space or lumen of a cap or collet 316/416. The first strut arms 214/114 are free and unconstrained by such a cap. Although four struts 212/112 are illustrated in these figures, it is possible to construct device halves with 2, 3, 5, 6, 8, 10, 12, or another number of struts per device half.

Figure 6E:
FIG. 6E is a view of two device halves coming together to form a full device, the forked ends of the struts being placed within the collet, in accordance with another embodiment of the present invention.
Figure 6F:
FIG. 6F is a view of two device halves coming together to form a full device, the non-forked (or single) ends of the struts being placed within the collet, in accordance with another embodiment of the present invention.

FIGS. 6E and 6F show how the device halves of FIGS. 6C and 6D merge to become a single device. In the case of FIG. 6E, the first arms 212 are constrained within the collets of the device halves and the secondary arms have free ends. The device halves are positioned opposite one another. The device halves are arranged such that when the tensioner is pulled and the device halves merge, the secondary strut arms will interlock, their forking points substantially aligning radially. In such an arrangement the secondary strut arms will make contact either substantially at the forking point, in the case of the U-shaped arms, or along some or all of the length of the secondary strut arms, such as in the V-shaped arms. In an embodiment where both device halves have the same number of struts, one device half is rotated slightly in such a way to facilitate such interlocking. In another embodiment, one device half may have one more forked arm than the one with which it pairs.

In the embodiment of FIG. 6F, the first strut arms 114 are not constrained by the collet now fit within the collet of the opposite device half or, alternatively, move into place outside of the opposite collet. As the device halves merge together, the second strut arms 215/115 approach one another and meet at the forking points 213/113. When the forking points 213/113 collide and a longitudinal force continues to be applied to the device by a tensioner element, an outward radial force is created and the device expands radially as a result. The tensioner element may be used as described above to lock the devices of FIGS. 6E and 6F into place.

There are many modifications that could be made to the above-described embodiment. Other ways of achieving the function may be envisaged. For example, instead of V-shaped struts, the struts may take on a closed triangular shape, with an extra crossbar across the top of the V-shape.

In another embodiment, the struts 12 may have a single straight leg and may be formed with locking bumps at one or more places along the lengths of the strut arms.

Referring now to materials for creating a biodegradable device, they can be fabricated from biocompatible materials. The devices are to be delivered with limited vessel trauma, and, in some embodiments, can possess the ability to break down entrapped emboli.

Some biodegradable materials can comprise a matrix which expands upon delivery. The device must capable of withstanding in vivo pressures, such as those created by heartbeat, breathing, blood pressure, and general movement of the patient in order to minimize movement. In some cases, the device 20 is capable of delivering thrombolytic agents in a controlled fashion.

The devices such as filtration devices described herein generally comprise one or more polymers. In some embodiments, at least one polymer can be an expandable polymer. Of particular interest are polymers that can be compressed as compression can impart the radial force 35 that assists in maintaining position and patency.

Various suitable polymers can be used including, for example, polyethers, polyesters, polyurethanes, and mixtures thereof. Compressed polymers are physically deformable or elastic such that they can be squeezed into a sheath or the like for delivery into a vessel of the patient, such that the polymer expands following removal from the sheath.

In some embodiments, the device comprises a plurality of polymers in a blend and/or a plurality of monomers in a copolymer, which can be a block copolymer.

Using a plurality of polymers includes the ability to introduce properties of each individual polymer or of each monomer group incorporated into a copolymer. In general, the expansion of the polymer and the corresponding device can occur spontaneously following the application of an appropriate stimulus. The appropriate stimulus can be, for example, contact with an aqueous fluid, release of constraining forces, such as applied by a sheath, and/or heating to body temperature.

The expandable nature of some polymers allows the device 20 to conform to the patient's vessel. Thus, minor variation in the vessel size and shape along the extent of the device can be handled appropriately by minor variations in the expansion of the device at different locations.

Biodegradable polymers and their degradative byproducts should be non-toxic, capable of maintaining good mechanical integrity until degraded, and capable of controlled rates of degradation. Suitable polymers preferably do not elicit an immune response.

Degradation generally proceeds by hydrolytic processes. Factors controlling the rate of degradation include but are not limited to molecular weight and hydrophobicity of the polymers. The degradation rate can depend on the location in the body.

One polymer that can be used exclusively or preferably as a copolymer is polylactic acid (PLA). PLA can be processed by extrusion, injection molding, film or sheet casting, and spinning. Thus, construction of struts 12 can be achieved in a number of ways.

Another polymeric substance that can be employed is poly(lactic-co-glycolic) acid (PLGA.) PLGA has been successful as a biodegradable polymer because it undergoes hydrolysis in the body to produce the original monomers, lactic acid and glycolic acid. These two monomers under normal physiological conditions, are byproducts of various metabolic pathways of the body. There is minimal systemic toxicity associated with using PLGA for drug delivery or biomaterial applications. Depending on the ratio of lactide to glycolide used for the polymerization, different properties of PLGA can be obtained. The lactide to glycolide ratio dictates stiffness, degradation time, flexibility, and other properties. The higher the content of glycolide units, the lower the time required for degradation. An exception to this rule is the copolymer with 50:50 monomers' ratio which exhibits the faster degradation (about two months). In addition, polymers that are end-capped with esters (as opposed to free carboxylic acid) demonstrate longer degradation half-lives.

The device can in some aspects be used to provide temporary filtration. However, as mentioned above, the ratio of lactide to glycolide can be adjusted to create a polymer that has a relatively long half-life after deployment. Short-term and long-term implants are envisioned in using these biodegradable implants.

Another class of material that can be used in the manufacture of a device with the properties described herein is a biodegradable polyurethane or polyurethaneurea. A biodegradable polyurethane can be formed in many ways. One type of monomer that can be used as a starting material in the manufacture of a suitable polyurethane is an isocyanate-based molecule. One type of isocyanate is an aliphatic diisocyanate, including but not limited to 1,4-butanediisocyanate, 1,6-hexamethylene diisocyanate, 2,2,4-trimethyl hexamethylene diisocyanate, ethyl 2,6-diisocyanatohexanoate, methyl 2,6-diisocyanatohexanoate, isophorone diisocyanate, and 1,4-cyclohexane diisocyanate. Polyols can also be used, including but not limited to poly(ethylene oxide), poly(tetramethylene oxide), poly(propylene oxide), poly (propylene oxide), poly(D,L-lactide), poly(epsilon-caprolactone), poly(glycolide), poly(propylene fumarate), and combinations thereof such as poly(lactic acid-ethyleneglycol-co-lactic acid). Such polyurethanes can be formulated using chain extending molecules including but not limited to ethylene glycol, 1,4-butanediol, 1,4-cyclohexanedimethanol, 1,2-ethanediamine, 1,4-butanediamine, 2-amino-1-butanol, 2-hydroxyethyl-2-hydroxypropanoate, 4-((1-(1-amino-2-phenylethoxy)ethoxy)methylcyclohexyl)methyl-2-amino-3-phenylpropanoate, 1,1-(hexane-1,6-diyl)bis(3-(2-hydroxyethyl)urea), ethane-1,2-diyl bis(3-(4-hydroxyphenyl)propanoate), bis(2-hydroxyethyl)phosphate, and bis(2-hydroxyhexyl) phosphate.

The struts of the device could further include attachment aids in order to maintain attachment to the vessel wall and patency of the device. For instance, small barbs could be attached to the periphery of the device. An advantage of including barbs that engage the vessel wall is that the barbs not only assist in fixing the device in place, but also irritate the vessel wall. This promotes restenosis, which in turn assists in providing improved fixation of the device within the blood vessel, and improved occlusion. The barbs could be relatively blunt in order to avoid piercing the vessel wall upon radial expansion. A purified extracellular matrix (ECM) material might be employed over some or all of the device in order to further encourage ingrowth of tissue into the device, thereby fixing it within the vessel.

The device could also serve to deliver a substance such as a drug to the area in which it has been deployed. In one embodiment, the struts of the device are coated with a polymeric coating. The polymeric coating may be porous and a drug to be delivered may be in the pores. In another embodiment, the struts themselves may be impregnated with a drug, the drug being released as the device degrades.

While the present invention has been described in terms of preferred embodiments, it will be understood, of course, that the invention is not limited thereto since modifications may be made to those skilled in the art, particularly in light of the foregoing teachings.

The invention claimed is:

1. A medical device for implantation in a body vessel comprising:
   a first collet comprising a first tube and a first cap, the first tube having a first tube end and extending to a second tube end, and a lumen formed through the first tube end to the second tube end, the first cap having an interior surface and being attached to the first tube end;
   a first device half having a proximal end and a distal end opposite the proximal end and defining a longitudinal axis therethrough, the first device half comprising a plurality of struts having a first arm and a pair of secondary arms connected to the first arm, each first arm having a first end disposed at the proximal end of the first device half, the first arms being arranged along the interior surface of the first cap substantially circumferentially, the first arm extending substantially parallel to the longitudinal axis to a second end, each secondary arm having a third end connected to the second end of the first arm and extending to a fourth end, the secondary arms being arranged to form a substantially cylindrical first device half;
   a second collet comprising a second tube and a second cap, the second tube having a first tube end and extending to a second tube end, and a lumen formed through the first tube end to the second tube end, the second cap being attached to the first tube end, the second cap having an aperture formed therethrough;
   a second device half having a proximal end and a distal end opposite the proximal end and defining a longitudinal axis therethrough, the second device half comprising a plurality of struts having a first arm and a pair of secondary arms connected to the first arm, each first arm having a first end disposed at the distal end of the second device half, the first arms being arranged along the interior surface of the second cap substantially circumferentially, the first arm extending substantially parallel to the longitudinal axis to a second end, each secondary arm having a third end connected to the second end of the first arm and extending to a fourth end, the secondary arms being arranged to form a substantially cylindrical second device half; and
   a tensioner having a first end and a second end, the first end of the tensioner being attached to the interior surface of the first cap, the tensioner extending to the second end through the aperture of the second collet.

2. The medical device of claim 1 wherein the first device half and the second device half are arranged such that as the device halves are moved longitudinally closer to each other, a portion of the secondary arms of the first device half contacts a portion of the secondary arms of the second device half to comprise a locking interface.

3. The medical device of claim 1 wherein the struts comprise a polymer.

4. The medical device of claim 3 wherein the polymer comprises at least one of a biodegradable polyester, polyether, or polyurethane.

5. The medical device of claim 1 wherein the first collet and the second collet each comprise a biodegradable polymer.

6. The medical device of claim 1 wherein the second collet further comprises a tensioner-retaining groove for retaining a portion of the tensioner.

7. A medical device for implantation in a body vessel comprising:
- a first collet comprising a first tube and a first cap, the first tube having a first tube end and extending to a second tube end, and a lumen formed through the first tube end to the second tube end, the first cap having an interior surface and being attached to the first tube end;
- a first device half having a proximal end and a distal end opposite the proximal end and defining a longitudinal axis therethrough, the first device half comprising a plurality of struts having a first arm and a pair of secondary arms connected to the first arm, each secondary arm having a first end disposed at the proximal end of the first device half, the first arms being arranged along the interior surface of the first cap substantially circumferentially, each secondary arm extending to a third end, each third end of a secondary arm of a strut being connected to the other third end, the third ends of the secondary arms of a strut being connected to the first end of the first arm, the first arm extending substantially parallel to the longitudinal axis to a second end to form a substantially cylindrical first device half;
- a second collet comprising a second tube and a second cap, the second tube having a first tube end and extending to a second tube end, and a lumen formed through the first tube end to the second tube end, the second cap being attached to the first tube end, the second cap having an aperture formed therethrough;
- a second device half having a proximal end and a distal end opposite the proximal end and defining a longitudinal axis therethrough, the second device half comprising a plurality of struts having a first arm and a pair of secondary arms connected to the first arm, each secondary arm having a first end disposed at the distal end of the second device half, the first arms being arranged along the interior surface of the second cap substantially circumferentially, each secondary arm extending to a third end, each third end of a secondary arm of a strut being connected to the other third end, the third ends of the secondary arms of a strut being connected to the first end of the first arm, the first arm extending substantially parallel to the longitudinal axis to a second end to form a substantially cylindrical second device half; and
- a tensioner having a first end and a second end, the first end of the tensioner being attached to the interior surface of the first cap, the tensioner extending to the second end through the aperture of the second collet.

8. The medical device of claim 7 wherein the first device half and the second device half are arranged such that as the device halves are moved longitudinally closer to each other, a portion of the secondary arms of the first device half contacts a portion of the secondary arms of the second device half to comprise a locking interface.

9. The medical device of claim 7 wherein the struts comprise a polymer.

10. The medical device of claim 9 wherein the polymer comprises at least one of a biodegradable polyester, polyether, or polyurethane.

11. The medical device of claim 7 wherein the first collet and the second collet each comprise a biodegradable polymer.

12. The medical device of claim 7 wherein the second collet further comprises a tensioner-retaining groove for retaining a portion of the tensioner.

\* \* \* \* \*